United States Patent
Shimizu

(10) Patent No.: US 9,775,507 B2
(45) Date of Patent: Oct. 3, 2017

(54) METHOD OF EVALUATING QUALITY OF VISION IN EXAMINEE'S EYE AND STORAGE MEDIUM

(71) Applicant: NIDEK CO., LTD., Gamagori-shi, Aichi (JP)

(72) Inventor: Kazunari Shimizu, Toyokawa (JP)

(73) Assignee: NIDEK CO., LTD., Gamagori (JP)

( * ) Notice: Subject to any disclaimer, the term of this patent is extended or adjusted under 35 U.S.C. 154(b) by 0 days.

(21) Appl. No.: 14/876,280

(22) Filed: Oct. 6, 2015

(65) Prior Publication Data

US 2016/0095512 A1   Apr. 7, 2016

(30) Foreign Application Priority Data

Oct. 7, 2014  (JP) ................. 2014-206372

(51) Int. Cl.
*A61B 3/10* (2006.01)
*A61B 3/00* (2006.01)
*A61B 3/04* (2006.01)
*A61B 3/103* (2006.01)

(52) U.S. Cl.
CPC .......... *A61B 3/0025* (2013.01); *A61B 3/0033* (2013.01); *A61B 3/0058* (2013.01); *A61B 3/04* (2013.01); *A61B 3/103* (2013.01); *A61B 3/1015* (2013.01)

(58) Field of Classification Search
CPC ....... A61B 3/0025; A61B 3/1015; A61B 3/04; A61B 3/0058; A61B 3/0033
USPC .................................................. 351/205, 246
See application file for complete search history.

(56) References Cited

FOREIGN PATENT DOCUMENTS

| JP | H10108837 A | 4/1998 |
|---|---|---|
| JP | H10216092 A | 8/1998 |
| JP | 2005211423 A | 8/2005 |
| JP | 2006149871 A | 6/2006 |
| WO | 2013151151 A1 | 10/2013 |

*Primary Examiner* — Jack Dinh
(74) *Attorney, Agent, or Firm* — Oliff PLC

(57) ABSTRACT

An ophthalmic apparatus obtains naked-eye wavefront aberration data of an examinee's eye measured by an aberration measuring unit, and calculates first corrected wavefront aberration data intended for a prescription with a first correction power based on the naked-eye wavefront aberration data and the first correction power and generates a first evaluation index based on the first corrected wavefront aberration data. The ophthalmic apparatus further calculates second corrected wavefront aberration data intended for a prescription with a second correction power different from the first correction power in at least one of spherical power, astigmatic power, and astigmatic axis angle based on the naked-eye wavefront aberration data and the second correction power, and generates a second evaluation index based on the second corrected wavefront aberration data. The ophthalmic apparatus then displays the first and second evaluation indexes selectively or in parallel on a monitor.

15 Claims, 7 Drawing Sheets

METHOD OF EVALUATING QUALITY OF VISION IN EXAMINEE'S EYE AND STORAGE MEDIUM

CROSS-REFERENCE TO RELATED APPLICATIONS

This application is based upon and claims the benefit of priority from the prior Japanese Patent Application No. 2014-206372 filed on Oct. 7, 2014, the entire contents of which are incorporated herein by reference.

BACKGROUND

The present disclosure relates to a method of evaluating the vision (vision quality) in an examinee's eye and also to a storage medium.

There is known an optometric device for performing a subjective examination of an eye refractive power of an examinee's eye by selectively placing optical elements such as spherical lenses and cylinder lenses in combination in front of the examinee's eye and directing the examinee's eye to look at a target(s) or optotype(s) presented before the eye (see WO2013/151151).

There is also known an apparatus for measuring wavefront aberration of an examinee's eye (especially, high-order aberration component) by projecting a spot-shaped light beam onto a fundus of the examinee's eye and detecting wavefront information of reflection light from the fundus. Further, simulating a retinal image based on wavefront aberration data obtained by the above type of apparatus has been proposed. For example, JP-A-2005-211423 discloses that a retinal image intended for a prescription based on a result of a subjective examination is simulated by use of a prescription with subjective values and wavefront aberration data of an examinee's eye.

SUMMARY

However, an examiner could not objectively grasp differences in visibility of the target(s) or optotype(s) according to changes of the optical elements to be placed during the subjective examination. Accordingly, in some cases (e.g., in a case of an irregular astigmatic eye), it is difficult to find an appropriate prescription value in the subjective examination.

The present disclosure has been made in consideration of the conventional problems and has a purpose of providing a method of evaluating the vision (vision quality) in an examinee's eye to smoothly obtain an appropriate prescription value in a subjective examination, and a storage medium.

To achieve the above purpose, one aspect of the present disclosure provides a method of evaluating quality of vision in an examinee's eye, comprising: an aberration data obtaining step of obtaining naked-eye wavefront aberration data of the examinee's eye measured by an ocular aberrometer; a first evaluation index generating step of: calculating, based on the naked-eye wavefront aberration data and a first correction power, first corrected wavefront aberration data of the examinee's eye intended for a prescription with the first correction power; and generating a first evaluation index based on the first corrected wavefront aberration data, the first evaluation index representing the quality of vision in the examinee's eye intended for the prescription with the first correction power; a second evaluation index generating step of: calculating, based on the naked-eye wavefront aberration data and a second correction power, second corrected wavefront aberration data of the examinee's eye intended for a prescription with the second correction power, the second correction power being different from the first correction power in at least one component of spherical power (S), astigmatic power (C), and astigmatic axis angle (A); and generating a second evaluation index based on the second corrected wavefront aberration data, the second evaluation index representing the quality of vision in the examinee's eye intended for the prescription with the second correction power; and a display control step of displaying the first evaluation index and the second evaluation index selectively or in parallel on a monitor.

DETAILED DESCRIPTION OF THE EXEMPLARY EMBODIMENTS

First Embodiment

Figure 1:
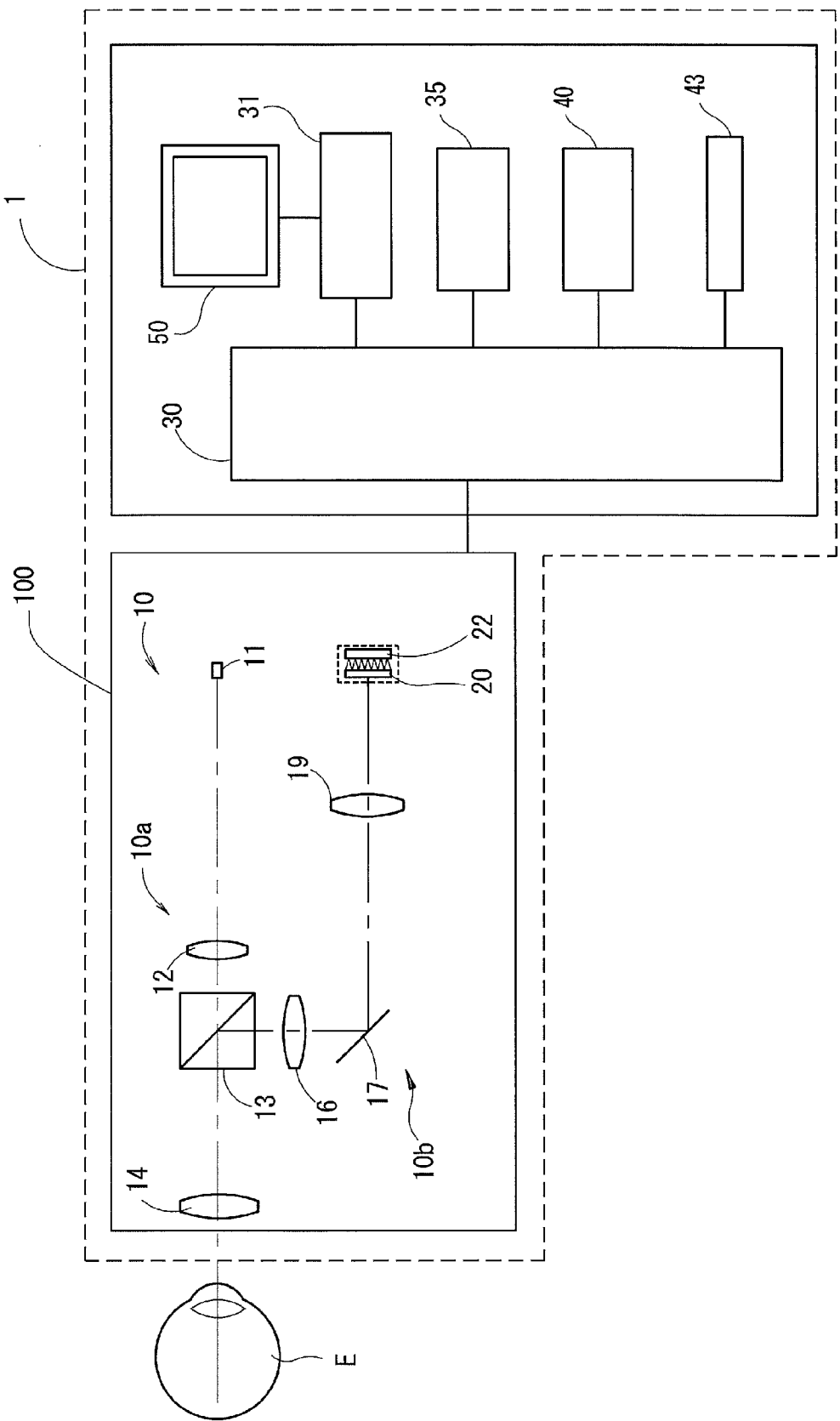
FIG. 1 is a schematic configuration view to explain structures of optical systems and a control system of an ophthalmic apparatus in a first embodiment.

An exemplificative embodiment of the present disclosure will now be given referring to the accompanying drawings. FIG. 1 is a block diagram showing a schematic structure of an ophthalmic apparatus 1 in a first embodiment. This ophthalmic apparatus 1, whose details will be described later, is configured to calculate an evaluation index for evaluation of the quality of vision (also referred to as the quality of vision degree) in an examinee's eye E by use of naked-eye wavefront aberration data of the examinee's eye. The ophthalmic apparatus 1 in the first embodiment may be integrated with a wavefront aberration measuring device (also called an ocular aberrometer).

In the first embodiment, the ophthalmic apparatus 1 includes a CPU (a processor) 30, a memory 35, an input interface 40, a printer 43, a monitor 50, an image processing part (a processor for image processing) 31, and others. These parts are connected via bus or the like.

The CPU 30 is a processor configured to control operations of each of the foregoing parts based on a retinal image simulation program and various control programs. The input interface 40 is an input device to be operated by an examiner. The input interface 40 may be selected from among a switch, a keyboard, a mouse, a pointing device such as a touch panel, and others. The image processing part 31 is configured to control a display screen of the monitor 50 for displaying thereon various data, a simulation image, and others. The CPU 30 may double as the image processing part 31. The memory 35 is a storage part which stores various programs (various control programs, ophthalmic measurement programs for operations of the apparatus) to be executed by the CPU 30. The memory 35 is used as a storage device and may be selected for example from among a semiconductor memory, a magnetic storage device, an optical storage device, and others. The monitor 50 is used as an output device and controlled by the CPU 30. The monitor 50 in this example is a touch panel enabling an examiner to input operations and doubles as at least part of the input interface 40. The printer 43 prints out a simulation result.

The ophthalmic apparatus 1 in the first embodiment includes an aberration measuring unit 100. This aberration measuring unit 100 is utilized to measure wavefront aberration of an examinee's eye E. The aberration measuring unit 100 has a structure of projecting a measurement target to a fundus of the examinee's eye and receiving reflection light of the measurement target from the fundus.

A measurement optical system 10 includes a light projecting optical system 10a and a light receiving optical system 10b. The light projecting optical system 10a is configured for example to project a spot-shaped light beam from a measurement light source to the fundus of the examinee's eye. The light receiving optical system 10b is configured for example to split the light beam reflected by the fundus, emerging from the examinee's eye E, into a plurality of light beams which will be received by a two-dimensional light receiving element 22. The ophthalmic apparatus 1 in the present embodiment measures the wavefront aberration of the examinee's eye based on outputs from the two-dimensional light receiving element 22.

To be concrete, the light projecting optical system 10a includes a relay lens 12 and an objective lens 14 arranged in the order from the measurement light source 11. The measurement light source 11 is placed in a position conjugate with the fundus of the examinee's eye. The light receiving optical system 10b includes, in the order from the front of the examinee's eye, the objective lens 14, a half mirror 13, a relay lens 16, a total reflection mirror 17, a collimator lens 19, a microlens array 20, and the two-dimensional light receiving element 22. The light receiving optical system 10b is configured to place the lens array 20 in an optically nearly conjugate relation with a pupil of the examinee's eye. The microlens array 20 is made up of microlenses (lenslets) two-dimensionally arranged on a plane perpendicular to the axis of measurement light, and a light shielding plate, and configured to split the fundus reflection light into a plurality of light beams (JP-A-10-216092(1998)). The foregoing structure uses a so-called Shack-Hartmann wavefront sensor. As an alternative, a so-called Talbot wavefront sensor may be used, in which an orthogonal grid mask is placed in a position conjugated with the pupil, and the light having passed through the mask is received by a two-dimensional light receiving element (for the details, see JP-A-2006-149871 filed by the present applicant).

The light beam emitted from the measurement light source 11 is projected onto the fundus of the examinee's eye via the relay lens 12, the objective lens 14, and the examinee's pupil. Accordingly, a point light image is formed on the fundus of the examinee's eye.

The point light image projected on the fundus of the examinee's eye emerges as reflection light from the examinee's eye and then is condensed by the objective lens 14 and reflected by the half mirror 13. The light reflected by the half mirror 13 is condensed once by the relay lens 16 and then reflected by the total reflection mirror 17. The light beam reflected by the total reflection mirror 17 passes through the collimator lens 19 and is split by the lens array 20 into a plurality of light beams, which are received by the two-dimensional light receiving element 22. A pattern image received by the two-dimensional light receiving element 22 is stored as image data in the memory 35.

The pattern image formed of the light split into the plurality of light beams by the lens array 20 and received by the two-dimensional light receiving element 22 will change according to the influence of aberration of the examinee's eye (low-order aberration, high-order aberration). The wavefront aberration of an examinee's eye can be measured by analyzing a pattern image created by reflection light from the eye by comparison with a reference pattern image of when aberration-free light passes. Specifically, based on a deviation amount of each dot image of the pattern image obtained by the aberration measuring unit 100, the CPU 30 determines a wavefront aberration $W(\rho, \theta)$ in a whole examinee's eye in a naked-eye state. In this first embodiment, a value of the wavefront aberration thus determined is stored as wavefront aberration data of the naked eye (also referred to as naked-eye wavefront aberration) in the memory 35.

The aberration measuring unit 100 is not limited to the above-mentioned structure and may be configured as a well-known structure. As an alternative, the aberration measuring unit 100 may be configured to project a slit light beam onto a fundus of an examinee's eye and output a phase difference signal of when the reflection light beam from the fundus is detected by the light receiving element (see JP-A-10(1998)-108837)). In this case, wavefront aberration of the examinee's eye E is obtained as a processing result of a phase difference signal.

<Operations of the Apparatus>

Figure 2:
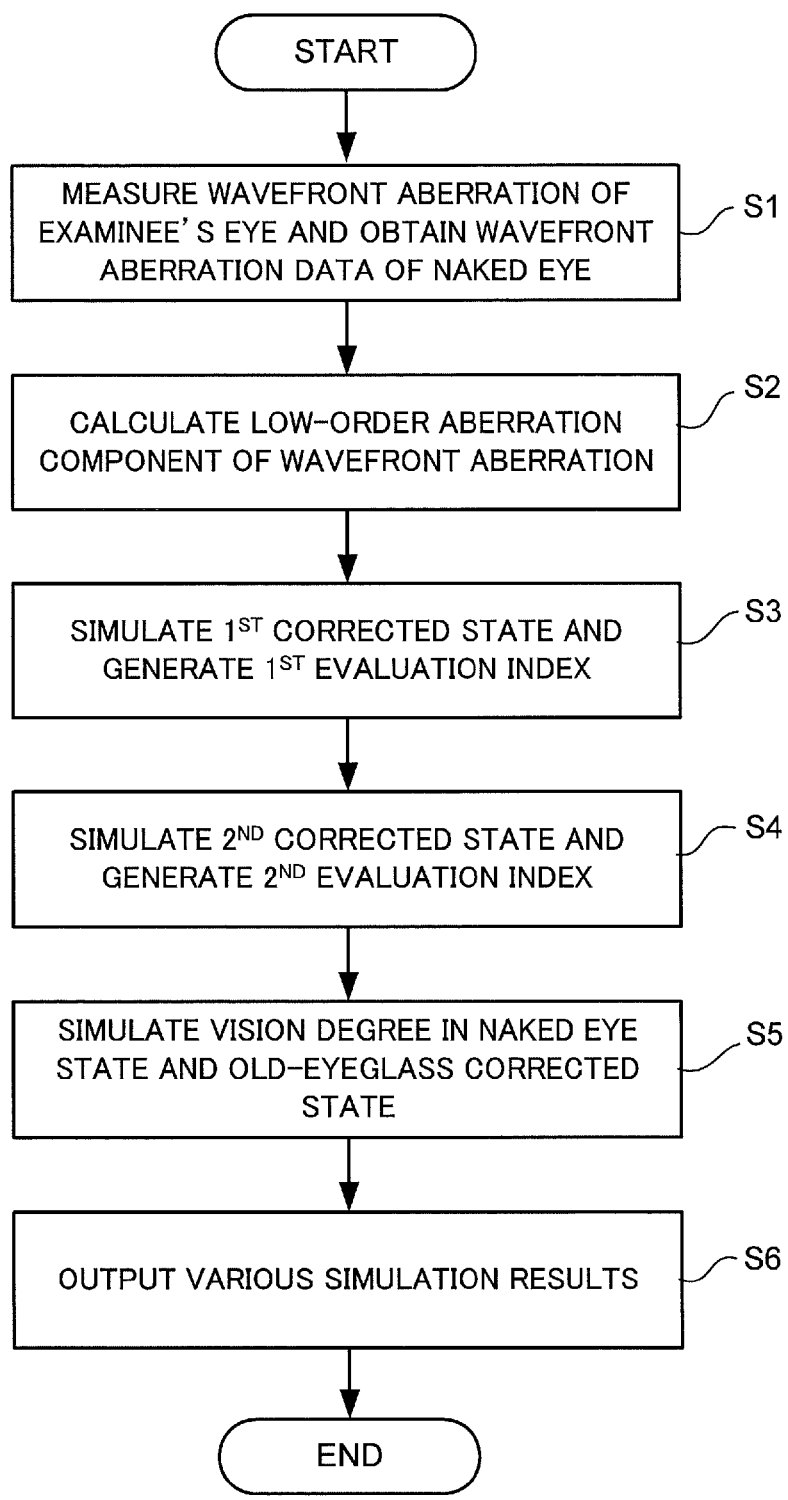
FIG. 2 is a flowchart showing a general outline of an ophthalmic measurement program in the first embodiment.

Next, operations of the ophthalmic apparatus 1 in the first embodiment will be explained, referring to a flowchart in FIG. 2.

The wavefront aberration of the examinee's eye E is first measured by use of the aberration measuring unit 100. The CPU 30 obtains the wavefront aberration of a whole examinee's eye in a naked-eye state (that is, naked-eye wavefront aberration $W(\rho, \theta)$) as naked-eye wavefront aberration data (S1). The obtained naked-eye wavefront aberration data is stored in the memory 35 by the CPU 30.

The CPU 30 then analyzes the naked-eye wavefront aberration data obtained by the aberration measuring unit 100. To be more specific, the CPU 30 calculates a low-order aberration component (to be more concrete, a second or lower order aberration component) of the naked-eye wavefront aberration $W(\rho, \theta)$ obtained in S1 (S2). The present embodiment exemplifies a case of calculating each component; spherical power (S), astigmatic power (C), and astigmatic axis angle (A). For instance, the CPU 30 determines the naked-eye wavefront aberration data of the examinee's eye corresponding to a predetermined pupil diameter region and further calculates the S, C, and A components of the naked-eye wavefront aberration $W(\rho, \theta)$ based on the low-order aberration component calculated from the naked-eye wavefront aberration data.

A method of calculating the S, C, and A components included in the naked-eye wavefront aberration $W(\rho, \theta)$ will be briefly explained below. The naked-eye wavefront aberration $W(\rho, \theta)$ is quantified by applying expansion of the known Zernike polynomial which is one of the polynomials used to approximate the naked-eye wavefront aberration data.

$$W(\rho,\theta) = \sum_{i=0}^{\infty} C_i Z_i \qquad \text{Eq. 1:}$$

In this equation, $Z_i$ is the i-th one of the Zernike terms, $C_i$ is a coefficient thereof, $\rho$ indicates a relative position (in a range of 0 to 1) with respect to a pupil diameter, and $\theta$ is an angle (0 to $2\pi$) measured counterclockwise with respect to an X axis. Further, a standardized display method provides the following equations.

$$W(\rho,\theta) = \sum_n \sum_m C_n^m Z_n^m(\rho,\theta)$$

$$Z_n^m(\rho,\theta) = N_n^m R_n^m(\rho)\cos m\theta;\ 0 \le m - N_n^m R_n^m(\rho)\sin m\theta;\ m < 0$$

$$R_n^m(\rho) = \sum_{s=0}^{(n-|m|)/2} \{(-1)^s (n-s)!/s![0.5(n+|m|)-s]![0.5(n-|m|)-s]!\}\rho^{m-2s}$$

A normalization constant is expressed as below:

$$N_n^m = \sqrt{2(n+1)/(1+\delta_{m0})} \qquad \text{Eq. 3:}$$

The spherical power (S), astigmatic power (C), and astigmatic axis angle (A) are expressed in terms of polynomials of degree 2 or less.

$$S = -4\sqrt{3} \cdot C_2^0 / R^2 \qquad \text{Eq. 4}$$

$$C = -4\sqrt{6} \cdot \sqrt{(C_2^{-2})^2 + (C_2^2)^2} / R^2$$

$$A = \tan^{-1}\left(\frac{C_2^{-2}}{C_2^2}\right) \cdot \frac{1}{2} \cdot \frac{180}{\pi} + 90$$

In this equation, R is the radius (mm) of a pupil diameter to be analyzed. A high-order aberration component is determined in terms of polynomials of degree 3 or higher.

For instance, when the naked-eye wavefront aberration $W(\rho,\theta)$ is to be determined by use of a value of a predetermined pupil diameter P and further the components S, C, and A are to be determined, R=P/2 is used. The CPU 30 may output the determined refractive values (SCA (REF)) of the examinee's eye on the monitor 50 (not shown).

<Subjective Examination Simulation>

Thereafter, the ophthalmic apparatus 1 in the first embodiment performs a simulation of the vision in the examinee's eye in the subjective examination conducted by use of an subjective optometric device such as a refractor. The subjective optometric device is an apparatus configured to switch the positions of optical members to be placed in front of the examinee's eye to subjectively measure a correction power for the examinee's eye. In this subjective examination, eye refractive power is subjectively measured based on whether an examinee can see targets or optotypes presented by a target presenting device, a visual acuity chart, or the like. In the first embodiment, in the simulation, the CPU 30 performs arithmetic processing using the naked-eye wavefront aberration data of the examinee's eye E to calculate the wavefront aberration data of the examinee's eye intended for the prescription with the correction power (hereinafter, referred to as "corrected wavefront aberration data"), based on the naked-eye wavefront aberration data and the correction power. As a result of this calculation, an evaluation index representing the quality of vision in the subjective examination is generated.

In the present embodiment, the CPU 30 applies a first correction power to the naked-eye wavefront aberration data to determine first corrected wavefront aberration data. Based on the first corrected wavefront aberration data, a first evaluation index intended for refraction correction with the first correction power is created. The CPU 30 further applies a second correction power to the naked-eye wavefront aberration data to determine second corrected wavefront aberration data. Based on the second corrected wavefront aberration data, a second evaluation index is generated (obtained). The second correction power is a correction power different by a predetermined amount from the first correction power. The correction power is a refractive power to be given to an examinee's eye to correct the naked eye refractive power thereof. The CPU 30 stores in the memory 35 the first evaluation index and the second evaluation index in association with each other.

The second correction power is different from the first correction power by a predetermined amount in any one of low-order aberration components up to second order (at least one of S, C, and A). As explained below, for instance, the first correction power and the second correction power may be different in only the astigmatic axis angle (A) among S, C, and A. In the first embodiment, a predetermined power corresponding to a difference between the first correction power and the second correction power is preferably a power associated with a step of examination in the subjective examination (that is, switching of examination power in the subjective optometric device). Further, two or more second correction powers may be set for one first correction power. When the two or more second correction powers are set, it may be arranged such that at least one of the second correction powers is a correction power (plus second correction power) in which any one component of S, C, A is increased by a predetermined amount with respect to the first correction power, and another second correction power is a correction power in which any one component of S, C, A is decreased by a predetermined amount with respect to the first correction power. In the first embodiment, for example, the second correction powers are set as both a power determined by rotating the astigmatic axis angle (A) by +5° and a power determined by rotating the astigmatic axis angle (A) by -5° with respect to the first correction power.

The evaluation index may be for example at least one of a simulation image of a retinal image of the examinee's eye in a refraction corrected state, and, an evaluation parameter representing the quality of vision in the examinee's eye in that state. The simulation image of the retinal image may also be a simulation image representing how a predetermined target is visible to the examinee's eye, for example. The evaluation parameter may be a Strehl ratio, an RMS value of wavefront aberration of a whole examinee's eye, a phase shift (PTF), a spatial frequency characteristic (MTF), and others.

In the present embodiment, for determining evaluation indexes each corresponding to correction powers, the CPU 30 determines the wavefront aberration data of the examinee's eye intended for the prescription with each correction power (hereinafter, referred to as "corrected wavefront aberration data") by calculation with the naked-eye wavefront aberration data of the whole examinee's eye (that is, the wavefront aberration data obtained by use of the aberration measuring unit 100). Herein, a general outline of a method of deriving the corrected wavefront aberration data will be explained as one example.

The CPU 30 determines the difference data in each meridian direction between low-order aberration component included in the naked-eye wavefront aberration data (naked-eye wavefront aberration $W(\rho,\theta)$) and correction power (Difference data=Low-order aberration component of naked-eye wavefront aberration W(ρ, θ)−Correction power; the "correction power" is for example a first correction power or a second correction power, which will be described later). The CPU 30 back calculates the wavefront aberration data by use of a polynomial with a coefficient corresponding to the difference data, substituted for a coefficient corresponding to low-order aberration (more specifically, low-order aberration up to second order) among the coefficients of the polynomials that approximate the naked-eye wavefront aberration data, and consequently obtains the corrected wavefront aberration data. A typical one of the polynomials that approximate the wavefront aberration data is the Zernike polynomial. The present disclosure is not limited thereto and may of course adopt any expressions that approximate wavefront aberration. In the first embodiment, for simulation of refraction correction related to the S, C, and A components, the difference data between the S, C, and A components of the naked-eye wavefront aberration W(ρ, θ) and the correction power is utilized.

More specifically, the difference data can be obtained based on a difference between approximate curves generated by converting each of the low-order aberration components of the naked-eye wavefront aberration W(ρ, θ) and the correction powers into an approximate curve (approximate curve representing distribution of eye refractive power (D) in each meridian direction (θ)). Each of the approximate curves is for example expressed as a sin curve. In the first embodiment, the CPU 30 substitutes the difference data (SCA difference) into SCA in quadratic expressions of the Zernike polynomial. As a result, coefficients of the quadratic expressions are calculated based on the difference data (SCA difference).

The CPU 30 in the first embodiment back calculates the wavefront aberration data by use of the Zernike coefficient which is a coefficient based on the difference data (SCA difference) substituted for a quadratic coefficient among naked-eye Zernike coefficients. As a result of this back calculation, corrected wavefront aberration data may be obtained.

The CPU 30 creates evaluation indexes each corresponding to the correction powers as a result of further arithmetic processing using the corrected wavefront aberration data. For instance, a simulation image of a retinal image of the examinee's eye intended for the prescription with the correction power can be created in the following manner. The CPU 30 first determines a point spread function (PSF) by use of the corrected wavefront aberration data. The CPU 30 then subjects the obtained PSF and a predetermined target (e.g., ETDRS optotype, resolution chart, landscape chart) to image processing (convolution integral). As a result thereof, the CPU 30 can obtain a simulation image representing how the predetermined target is visible to the examinee's eye intended for the prescription with correction power.

<Simulation in REF Value Corrected State>

In the first embodiment, as the first evaluation index, an evaluation index intended for correction with a refractive value (the first correction power in the first embodiment) for correcting the naked eye refractive power is generated based on arithmetic processing using the naked-eye wavefront aberration data (S3). In the first embodiment, specifically, an objective eye refractive value (REF value) based on the naked-eye wavefront aberration data is applied to the first correction power to create the first evaluation index. The REF value is an objective value of the correction power obtained in an objective examination and is determined from the S, C, and A components included in the naked-eye wavefront aberration W(ρ, θ) in the first embodiment. More concretely, the first evaluation index includes a simulation image representing the visibility of a predetermined target to the eye when a prescription for the eye is prepared with the REF value, and a Strehl ratio (one example of the evaluation parameter).

Herein, the CPU 30 determines for example the corrected wavefront aberration data of the examinee's eye intended for the prescription with the REF value in the foregoing manner. As a result thereof, the corrected wavefront aberration data is obtained based on a polynomial with a coefficient corresponding to the case where the S, C and A components are all zero, substituted for the Zernike polynomials for the naked eye. The CPU 30 acquires the simulation image related to the REF value based on the corrected wavefront aberration data intended for the prescription with the first correction power.

The Strehl ratio in the first embodiment may be an approximate value determined by the following equation:

$$SR = 1 - \left(\frac{2\pi}{\lambda}\right)^2 W^2 \qquad \text{Eq. 5}$$

where W is an RMS value of the naked-eye wavefront aberration W(ρ, θ). The Strehl value of the examinee's eye intended by the prescription with the REF value is obtained by substituting W with the RMS value based on the Zernike coefficient which is the substituted coefficient corresponding to the case where the S, C, and A are all zero. As the Strehl ratio is closer to 1, the aberration is less, indicating good contrast of the examinee's eye.

In the first embodiment, the simulation image and the Strehl ratio obtained as above are output and displayed on the monitor 50 in later step S6.

<Simulation in Second Corrected State>

The CPU 30 generates a second evaluation index representing the vision in the examinee's eye when a prescription for the eye with the second correction power is prepared (S4). In the first embodiment, the correction power determined by adding a predetermined SCA component(s) to the objective eye refractive value (REF value) is applied to the second correction power, and thereby the second evaluation index is created. The "adding" herein includes increasing any of the SCA components and decreasing any of the SCA components. In the first embodiment, two kinds of evaluation indexes, plus second evaluation index and minus second evaluation index, are created as the second evaluation indexes. The plus second evaluation index represents the vision intended by the prescription with the correction power having the astigmatic axis angle (A) further rotated +5° (that is, changed in an increasing direction) with respect to the first correction power (the REF value in the first embodiment). The minus second evaluation index represents the vision intended by the prescription with the correction power having the astigmatic axis angle (A) further rotated −5° (that is, changed in a decreasing direction) with respect to the first correction power. In the first embodiment, as the plus second evaluation index and the minus second evaluation index, the simulation image and the Strehl ratio (one example of the evaluation parameter) related to respective correction powers are created.

Accordingly, the CPU 30 determines the corrected wavefront aberration data of the examinee's eye intended for the prescription with the correction power having the astigmatic axis angle (A) rotated plus or minus 5° with respect to the refractive value. Based on the corrected wavefront aberration data intended for the prescription with each correction power, the CPU 30 creates simulation images related to respective second correction powers. As a result, it is possible to obtain a simulation image of a predetermined target image to be formed on a retinal surface of the examinee's eye when a prescription for the eye is prepared with the correction power different by a predetermined amount from the refractive value. That is, the CPU 30 obtains the simulation image related to the correction power different by the predetermined amount from the refractive value.

Further, the CPU 30 in the first embodiment determines the Strehl ratio by use of Eq. 5. In this case, W in Eq. 5 is substituted with an RMS value of the whole aberration based on an expression with a coefficient based on the difference data (SCA difference) between the S, C, and A data components included in the naked-eye wavefront aberration $W(\rho, \theta)$ and the second correction power, substituted for a coefficient of a quadratic expression, among the Zernike polynomials that approximate the naked-eye wavefront aberration data.

<Simulation in Naked-Eye State and Old Eyeglass Corrected State>

In the first embodiment, the CPU 30 may obtain at least one of a simulation image of the vision in a naked eye and a simulation image of the vision in an old-eyeglass corrected state (also referred to as a previous-eyeglass corrected state) (S5).

The simulation image of the vision in the naked eye can be obtained in such a way that the point spread function (PSF) in the naked-eye state is obtained by use of the naked-eye wavefront aberration data and this PSF and a predetermined target are subjected to the image processing. For the method of generating the simulation image of the vision in the old-eyeglass corrected state, for example, refer to WO2013/151151 mentioned above. A high-order aberration amount (HO) of the naked-eye wavefront aberration data may also be calculated. This high-order aberration amount (HO) may be for example an RMS value of the high-order aberration component in the wavefront aberration data. In this case, the high-order aberration amount (HO) can be calculated based on a third or higher order expressions of the Zernike polynomials.

<Display of Simulation Results>

Figure 3:
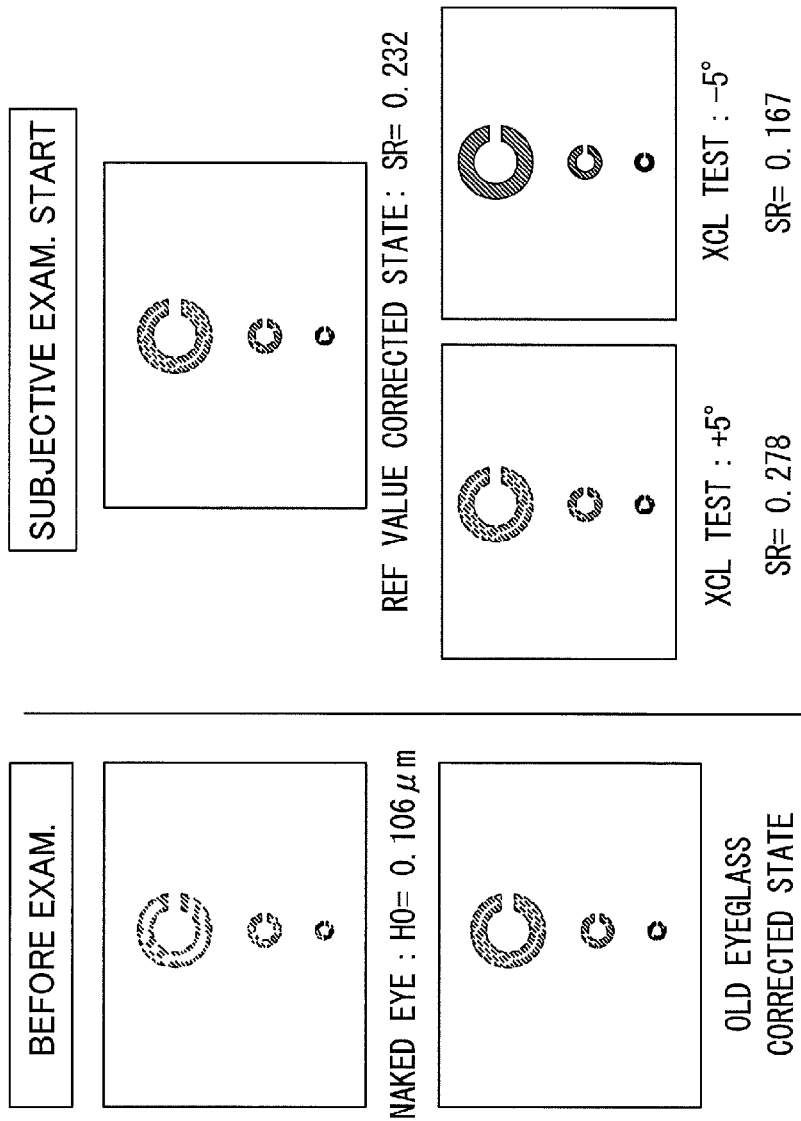
FIG. 3 shows one example of a display screen showing various simulation results obtained in the ophthalmic apparatus in the first embodiment.

In the first embodiment, the CPU 30 outputs and displays results of the various simulations (arithmetic processing) described above on the monitor 50. As shown in FIG. 3, on a simulation result screen of the monitor 50, for example, a first evaluation index (i.e. a simulation image in the REF value corrected state and a Strehl ratio in the REF value corrected state) and a second evaluation index (e.g. a predicted examination image (plus or minus 5° or less) and a Strehl ratio in the second corrected state) are displayed in parallel (concurrently). This enables an examiner to objectively recognize and further compare the vision in the examinee's eye in the refractive value corrected state initially set in the subjective examination and the vision in the examinee's eye of when the power value is changed by a predetermined amount with respect to the REF value corrected state. Accordingly, for instance, when the subjective examination is advanced to the second corrected state, the examiner can easily grasp whether the vision in the examinee's eye is improved. For instance, if receiving a response or an inquiry from an examinee when the position of the optical element(s) is changed over in the subjective examination, the examiner can appropriately make a reply and advance the examination. As a result, an adequate prescription value can be determined in the subjective examination.

Especially, even when the correction power obtained as an objective value is prescribed, an eye with irregular astigmatism such as an eye having a keratoconus cornea may not obtain appropriate vision. In this case, for example, the evaluation parameters (e.g. the Strehl ratios) indicating the vision in corrected states with two or more different astigmatic axis angles as shown in the first embodiment and the simulation images could become important clues to obtain a prescription value for appropriate vision. In the first embodiment, specifically, the examiner can determine a prescription value even for the eye with irregular astigmatism by advancing the examination using the first evaluation index and the second evaluation index as a guide.

In the first embodiment, furthermore, the second evaluation indexes related to the plurality of second correction powers are displayed on the monitor 50. To be concrete, the second evaluation index intended for the prescription with the astigmatic axis angle (A) rotated +5° with respect to the refractive value and the second evaluation index intended for the prescription with the astigmatic axis angle (A) rotated −5° with respect to the refractive value are displayed in parallel (concurrently). When the second evaluation indexes related to the plurality of second correction powers are displayed, for example, the examiner can more excellently predict a change in vision in the examinee in association with the progression of the subjective examination. In the present embodiment, moreover, the examiner can easily compare the vision assumed when the power of any one of S, C, and A (the astigmatic axis angle (A) in the first embodiment) is increased with respect to the refractive value corrected state and the vision assumed when the same is decreased. Accordingly, the examiner can predict well the examination procedures to improve the vision in the examinee's eye. Thus, the examiner can easily perform an appropriate subjective examination.

In the first embodiment, the simulation result of the vision in the examinee's eye in the naked-eye state and the simulation result of the vision in the old-eyeglass corrected state are displayed on the monitor 50 (see FIG. 3). This can facilitate planning of the examination including a subjective examination or predicting responses of the examinee in the subjective examination. For example, a value of the high-order aberration amount (HO) gives an indication of ease of improving the visual acuity by correction. When the high-order aberration amount (HO) is high, a transparent body of the examinee's eye may have opacity due to cataract or other causes. In this case, therefore, the examiner can also plan an examination for checking the opacity (e.g., an examination using a transillumination image).

Second Embodiment

A second embodiment in the present disclosure will be explained below. In this second embodiment, the evaluation indexes to be output by an ophthalmic apparatus to represent the quality of vision in an examinee's eye are switched from one to another in sync with progression of a subjective examination. Unless otherwise noted, the schematic structure of the ophthalmic apparatus 1 in the second embodiment is identical to that in the first embodiment and thus its explanation is omitted.

<Connection with Subjective Optometry Device>

Figure 4:
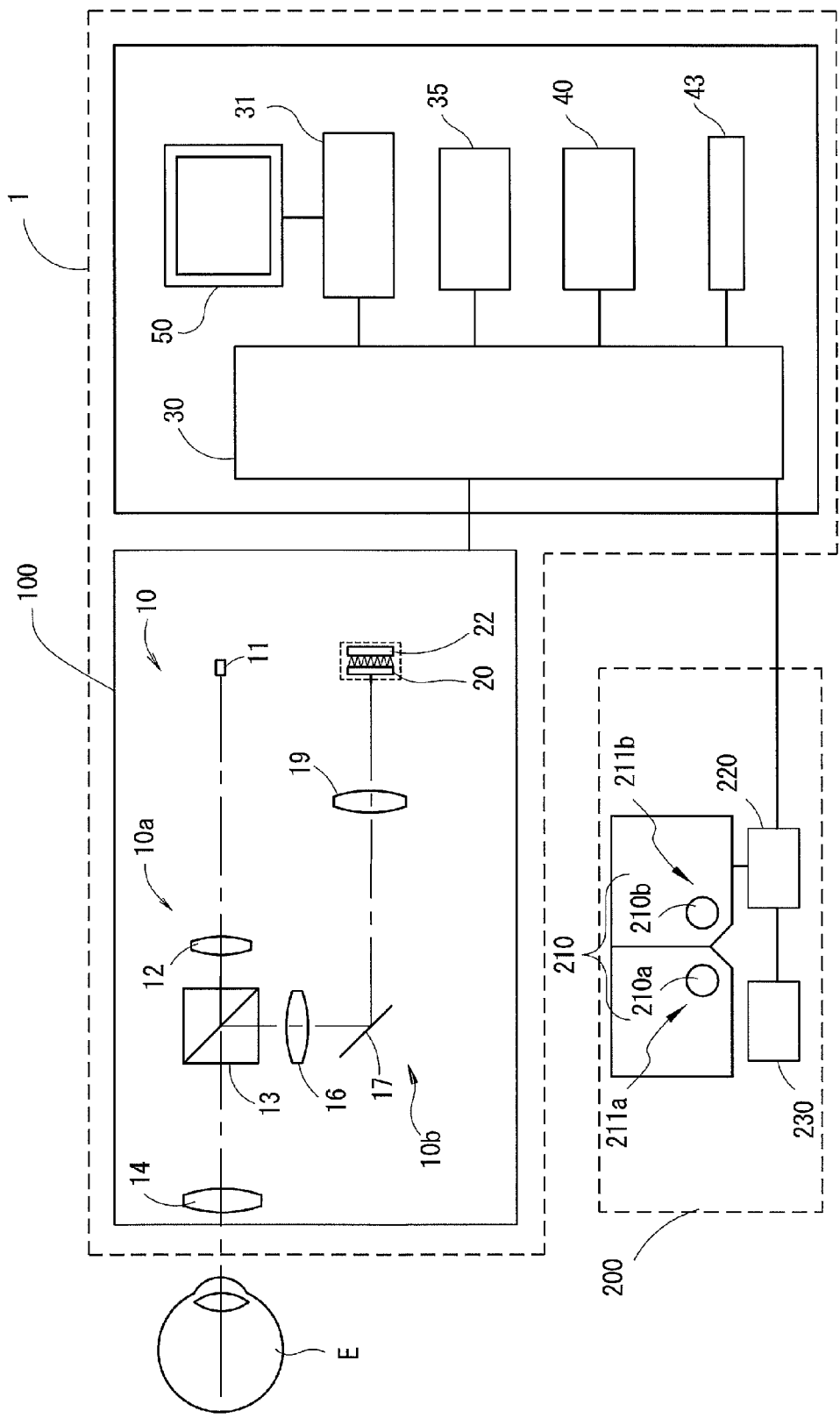
FIG. 4 is a schematic configuration view showing structures of an ophthalmic apparatus and an optometric device connected to the ophthalmic apparatus in a second embodiment.

In the second embodiment, as shown in FIG. 4, the ophthalmic apparatus 1 is connected to a subjective optometric device (hereinafter, simply referred to as an optometric device) 200. This optometric device 200 is mainly used to subjectively measure the refractive power of an examinee's eye.

In the second embodiment, the optometric device 200 includes a lens unit 210, a control box 220, and a controller 230.

The lens unit 210 includes a pair of left and right lens units 210a and 210b to be disposed in front of the examinee's eye during the subjective examination. Each of the lens units 210 includes lens disks each of which has various kinds of optical elements (spherical lenses, cylinder lenses, cross cylinder lenses, etc.) concyclically arranged, a first rotation drive part for rotating each lens disk itself, and a second rotation drive part for individually rotating the optical elements with respect to each corresponding lens disk. The optometric device 200 is used to perform the subjective examination by switching optical characteristics of the optical elements to be placed in examination windows 211a and 211b (that is, in front of the examinee's eye).

Figure 5:
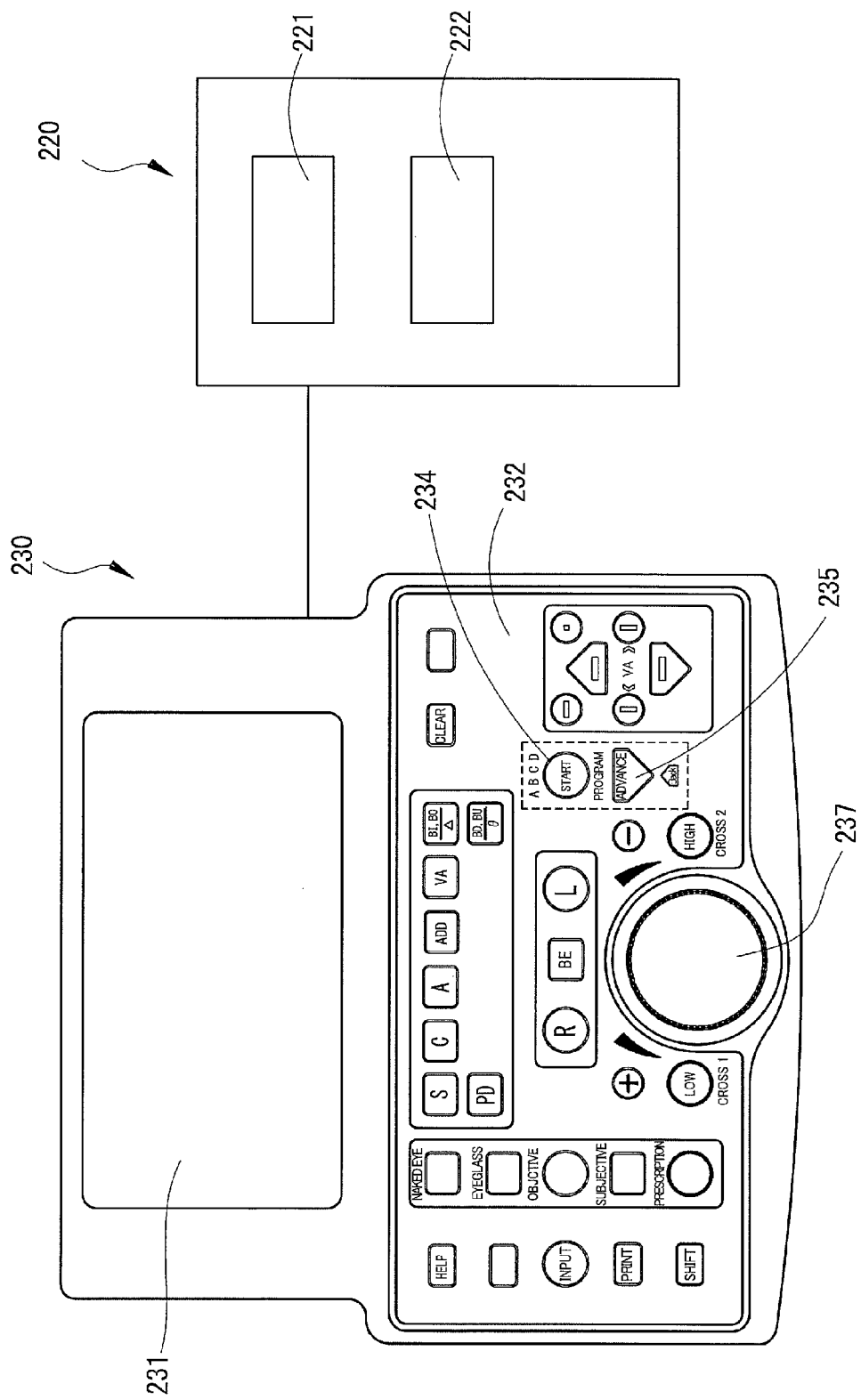
FIG. 5 is a diagram showing details of a controller and a control box of the optometric device.

The control box 220 includes, as shown in FIG. 5, at least a control part 221 and a memory 222. The control part 221 is a processor for controlling operations of the whole optometric device 200. The memory 222 stores a program to execute the subjective examination in the optometric device 200. Further, measurement results and others in the subjective examination may be stored in the memory 222.

In the second embodiment, the control box 220 of the optometric device 200 is connected to the CPU 30 of the ophthalmic apparatus 1 by wire or wirelessly. This configuration allows data communication (delivery) between the optometric device 200 and the ophthalmic apparatus 1. The optometric device 200 obtains a REF value (an objective value: expressed in e.g. spherical power (S), cylinder power (C), and astigmatic axis angle (A)) based on the naked-eye wavefront aberration $W(\rho, \theta)$ measured in the ophthalmic apparatus 1. The refractive value is stored in the memory 222. When the refractive value is obtained, the control part 221 of the optometric device 200 drives the lens unit 210 to bring the optical element corresponding to the refractive value, as an initial value, before the eye. Thereafter, the optometric device 200 performs the examination by switching the optical characteristics of the optical elements to be placed in front of the eye based on the obtained refractive value. The ophthalmic apparatus 1 can further obtain, from the control box 220, a subjective value obtained in the optometric device 200 and data and others related to progression of the subjective examination.

In the subjective examination, the optometric device 200 determines a perfect correction power to obtain a highest visual acuity of the examinee. Then, the optometric device 200 decides a final subjective value (an eyeglass prescription value) according to examinee's experiences or a predetermined method based on this perfect correction power.

The controller 230 is a unit to allow the examiner to operate the optometric device 200. As shown in FIG. 5, in the second embodiment, the controller 230 includes a display 231 and an input interface (a switch part in the present embodiment) 232. The display 231 displays thereon optometry information.

The switch part 232 is provided with a plurality of switches or buttons.

The switch part 232 may be configured as a touch panel to be shared by the display. The switch part 232 in the second embodiment is provided with for example a start switch 234, an advance switch 235, a rotating dial 237, and others. The rotating dial 237 is used to adjust the spherical power (S), the astigmatic power (C), axial angle of the astigmatic axis angle (A), and others.

<Operations of Apparatus>

Figure 6:
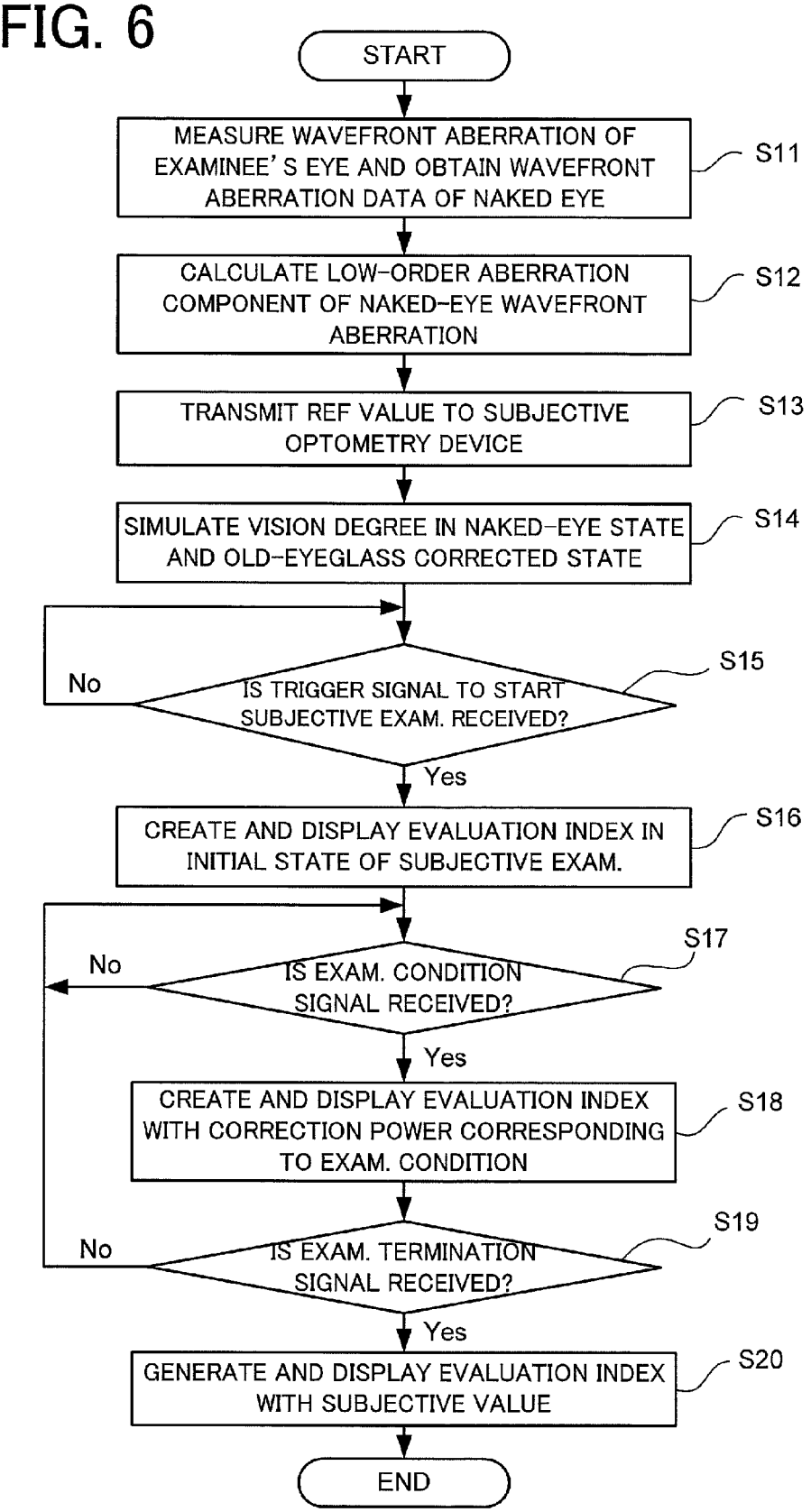
FIG. 6 is a flowchart showing a general outline of an ophthalmic measurement program in the second embodiment.

Operations of the ophthalmic apparatus 1 in the second embodiment will be explained below, referring to the flowchart of FIG. 6.

The ophthalmic apparatus 1 measures the wavefront aberration of the whole examinee's eye in a naked-eye state by use of the aberration measuring unit 100. As a result thereof, the naked-eye wavefront aberration data (wavefront aberration $W(\rho, \theta)$ in the present embodiment) is obtained (S11). The CPU 30 firstly stores the wavefront aberration data in the memory 35.

Subsequently, the CPU 30 analyzes the naked-eye wavefront aberration data obtained by the aberration measuring unit 100 and determines a low-order component (herein, the S, C, and A components) included in the naked-eye wavefront aberration $W(\rho, \theta)$ (S12).

Next, the CPU 30 transmits the REF value (objective value) based on the naked-eye wavefront aberration $W(\rho, \theta)$ to the optometric device 200 (S13). In this embodiment, values of the S, C, and A components of the naked-eye wavefront aberration $W(\rho, \theta)$ are transmitted as the REF value. The resultant REF value based on the wavefront aberration is stored in the memory 222 of the optometric device 200. The transmission of the REF value to the optometric device 200 may be performed in response to a REF-value request signal from the optometric device 200.

Figure 7:
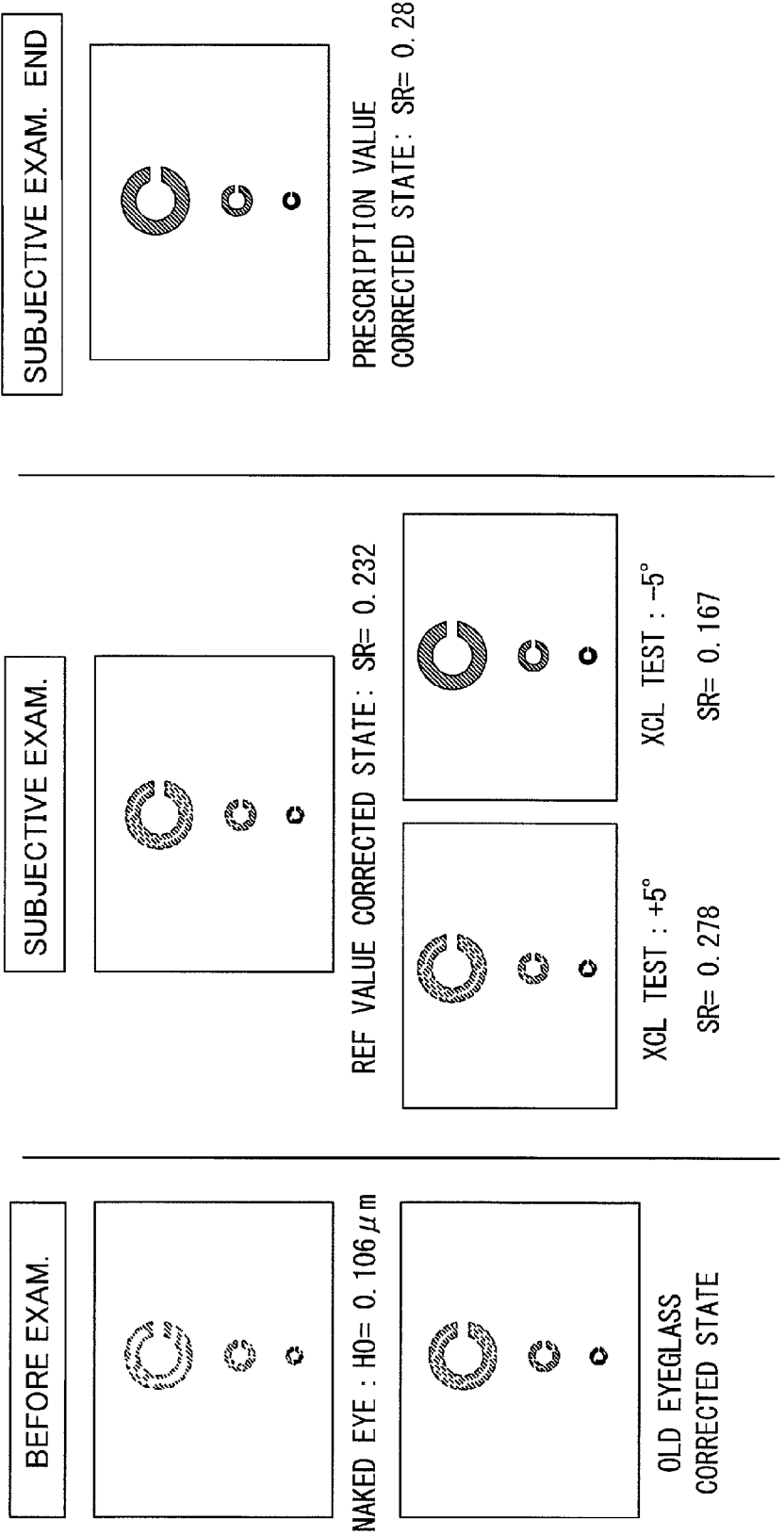
FIG. 7 shows one example of a display screen showing various simulation results obtained in the ophthalmic apparatus in the second embodiment.

At this stage, the CPU 30 may create at least one of a simulation image of the vision in the naked eye and a simulation image of the vision in an old-eyeglass corrected state (also referred to as a previous eyeglass corrected state) (S14). The created simulation image or images may be displayed on the monitor 50 (see FIG. 7). The following simulation result may be displayed on the display 231 provided in the controller 230 of the optometric device 200.

<Simulation in Subjective Examination>

In the second embodiment, similar to the first embodiment, an evaluation index representing the vision in the examinee's eye in the subjective examination is simulated by the ophthalmic apparatus 1. The CPU 30 in the second embodiment generates each evaluation index in sync with progression of the subjective examination (S15 to S20). For instance, the ophthalmic apparatus 1 in the second embodiment generates different evaluation indexes according to the examination conditions of the subjective examination set by use of the controller 230 of the optometric device 200. In this case, based on the wavefront aberration data and the correction power, the CPU 30 calculates the corrected wavefront aberration data representing the vision in the examinee's eye intended for the prescription with the correction power corresponding to the examination conditions set in the optometric device 200. Based on the calculated corrected wavefront aberration data, the CPU 30 then generates the evaluation index representing the vision in the examinee's eye intended for the prescription with the correction power. The examination conditions may be conditions on at least one of the kinds of optical members to be placed before the examinee's eye by the optometric device 200, axial angles of the optical members, and examination optotypes to be presented to the examinee's eye.

In the second embodiment, in a similar way to the first embodiment, for the first correction power and the second correction power that are different from each other in at least one of the S, C, and A components by a predetermined amount, the respective evaluation indexes may be generated.

In this case, the correction power corresponding to the examination conditions may be applied to the first correction power to generate the first evaluation index. Further, the correction power determined by adding a predetermined SCA component(s) to the correction power corresponding to the examination conditions may be applied to the second correction power to generate the second evaluation index. For example, the first evaluation index may be used to show the vision in the examinee's eye intended for the prescription with the power examined under the examination conditions currently set in the optometric device 200. In this case, the second evaluation index is presented to show the vision in the examinee's eye of when the power is changed by a predetermined value with respect to the power examined under the current examination conditions. The following explanation is given to a concrete example that the second evaluation index includes two kinds of evaluation indexes individually representing the degree of vision of when the astigmatic axis angle (A) is rotated +5° with respect to the first evaluation index and the degree of vision of when the astigmatic axis angle (A) is rotated −5°. Each of the evaluation indexes will be explained as a simulation image and a parameter of evaluating the degree of vision in a similar manner to in the first embodiment; however, the present disclosure is of course not limited thereto.

In the second embodiment, the ophthalmic apparatus 1 obtains examination condition data in the optometric device 200. For instance, the examination condition data is obtained based on operations of the controller 230. The examination condition data may be the data representing the examination conditions themselves set in the optometric device 200 or the data indicating the power to be examined under that examination conditions. In this embodiment, the examination condition data is the data representing at least a correction value of the astigmatic axis angle (A) corresponding to the examination conditions in the optometric device 200. The examination condition data may be the data to be transmitted from the optometric device 200 according to a setting operation of the examination conditions on the controller 230 or the data stored in advance in the memory 35 of the ophthalmic apparatus 1.

For instance, the CPU 30 transmits the REF value based on the naked-eye wavefront aberration W(ρ, θ) to the optometric device 200 and then determines whether a trigger signal to start the subjective examination has been input (S15), and puts the operation related to evaluation index in a standby state until the trigger signal is input (S15: No).

In the optometric device 200 in the present embodiment, when the start switch 234 is operated by the examiner, the trigger signal to start the subjective examination is output from the controller 230. Upon receipt of the trigger signal, the control part 221 of the optometric device 200 brings the optical element(s) corresponding to the refractive value stored in advance in the memory 222 into at least one of the examination windows 211a and 211b. The trigger signal is also transmitted to the ophthalmic apparatus 1. As a result, the CPU 30 releases the standby state (S15: Yes), generates the first and second evaluation indexes in an initial state of the subjective examination, and displays the generated evaluation indexes on the monitor 50 (S16). The CPU 30 further stores the first evaluation index and the second evaluation index in association with each other in the memory 35. In the initial state of the subjective examination, the REF value based on the naked-eye wavefront aberration W(ρ, θ) measured in advance by the ophthalmic apparatus 1 may be used as the examination condition data. Specifically, the evaluation index intended for correction with the REF value may be generated as the first evaluation index in the initial state of the subjective examination. The vision intended for the case where the astigmatic axis angle (A) is rotated by a predetermined amount with respect to the REF value may be generated as the second evaluation index in the initial state of the subjective examination. The timing of generating and starting display of the first evaluation index and the second evaluation index does not always have to wait for input of the trigger signal. For instance, generation of each evaluation index and others may be performed before input of the trigger signal.

On the other hand, after the optical element(s) corresponding to the REF value is disposed in front of the eye, the optometric device 200 may be used to execute an R/G test, for example. The examiner directs the examinee to look at a red-green optotype. In addition, the examination windows 211a and 211b are applied with a fogging to add S+0.5 D to the REF value. The control box 220 of the optometric device 200 is placed into a SPH mode allowing the spherical power to be changed according to the optometry program. The examiner operates the rotating dial 237 to adjust the spherical power so that the targets on a red background and a green background appear equally clear by receiving an answer from the examinee.

When the advance switch 235 is operated after adjustment of the spherical power, an astigmatic axis adjustment examination using an XC lens is followed. At this time, the examiner shows a point-group target to the examinee. The control part 221 further drives the lens unit 210 to place the XC lens in front of the examinee's eye. The control part 221 also drives a second drive mechanism not shown to adjust the minus axis of the XC lens according to the astigmatic axis angle of the objective value data (in the astigmatic axis adjustment examination, the minus axis of the XC lens is positioned at 45° with respect to the minus axis of the astigmatic lens placed in the examination window). The examiner operates the rotating dial 237 to adjust the angle of the XC lens about the lens optical axis (in steps of 5° per one operation, for example) while checking a difference in the visibility of the point-group target before and after the XC lens is rotated counterclockwise (turned counterclockwise about the meridian of the XC lens) based on a reply from the examinee, so that the visibility of the point-group target becomes equal before and after the rotation of the XC lens. In this case, a correction value of the astigmatic axis angle (A) corresponding to the examination condition is changed in steps of 5° according to the operation of the rotating dial 237. The optometric device 200 transmits an examination condition signal (e.g., a signal representing a correction value of the astigmatic axis angle (A) corresponding to that examination condition) to the ophthalmic apparatus 1 every time the rotating dial 237 is operated one step.

In the ophthalmic apparatus 1, for instance, after the initial display of the first evaluation index and the second evaluation index is performed in S16, those evaluation indexes may remain displayed on the monitor 50 until the examination condition signal is input (S17: No). Upon input of the examination condition signal, the evaluation indexes with correction values corresponding to a new examination condition(s) indicated by the examination condition signal are generated and displayed (S18). For instance, when the astigmatic axis angle (A) examined in the optometric device 200 is increased by 5° from the astigmatic axis angle (A) of the REF value which is an initial correction value in the subjective examination, the CPU 30 generates and displays the first and second evaluation indexes respectively representing the vision in the examinee's eye of when the first correction power and the second correction power are increased by 5° from the respective initial values (that is, the values in S16).

Thereafter, until the ophthalmic apparatus 1 receives an examination termination signal from the optometric device 200, the operations in S17 and S18 are repeated (S19: No). In the second embodiment, specifically, the CPU 30 updates the first evaluation index and the second evaluation index in sync with the examination conditions on the correction values of the astigmatic axis angle (A) examined in the subjective examination. As a result, in the subjective examination, the examiner can sequentially check differences in vision based on each evaluation index when the astigmatic axis angle (A) examined in the subjective examination is changed. Accordingly, the examiner can easily advance the subjective examination while recognizing the vision in the examinee's eye at each step.

After completion of each step of the subjective examination such as a follow-up red-green test, the examiner performs a predetermined examination terminating operation on the controller 230. As a result, the optometric device 200 transmits final subjective value data and an examination termination signal to the ophthalmic apparatus 1. The memory 222 of the optometric device 200 stores the subjective value data. When the ophthalmic apparatus 1 receives the examination termination signal (S19: Yes), the CPU 30 generates an evaluation index (see FIG. 7) representing the vision in the prescription-value corrected state intended for the prescription with the subjective value based on the subjective value data received from the optometric device 200 and displays the generated evaluation index on the monitor 50 (S20). Thus, the examiner can check the vision in the examinee's eye intended for the prescription with the final prescription value.

<Variations>

The present disclosure is described based on the foregoing embodiments; however, the embodiments may be variously modified or changed.

For instance, the above embodiment is explained with the first and second evaluation indexes to be displayed in parallel on the monitor 50. As an alternative, they may be selectively displayed by switching from one to another.

Each of the above embodiments is explained in which both the plus second evaluation index and the minus second evaluation index are generated and displayed as the second evaluation indexes by the ophthalmic apparatus 1. However, the present disclosure is not necessarily limited to such a configuration. Either one of the second evaluation indexes has only to be generated and displayed. Even when both the plus second evaluation index and the minus second evaluation index are generated, they are not necessarily displayed in parallel and may be selectively displayed.

In each of the above embodiments, the first evaluation index and the second evaluation index are explained as being different only in the astigmatic axis angle (A) by a predetermined amount among the correction powers intended for the prescription. As an alternative, they may be different in power other than the astigmatic axis angle (A) among the S, C, and A. For example, when the spherical power value (S) is different, it is conceived that, in an examination of adjusting the spherical power such as the foregoing red-green test, the spherical power can be easily adjusted to a suitable one for good vision.

In the second embodiment, only when the examination of the astigmatic axis angle (A) is performed in the subjective examination, the evaluation index (the first and second evaluation indexes) representing the vision in the subjective examination is updated in sync with the examination conditions in the optometric device 200 according to the operation on the controller 230. However, the present disclosure is not necessarily limited thereto. As an alternative, the evaluation index (first and second evaluation indexes) representing the vision in the subjective examination may be updated in sync with the examination conditions set in the optometric device 200 even for the examinations of the spherical power (S) and the astigmatic power (C) in the subjective examination.

In each of the above embodiments, the apparatus having the structure of an ocular aberrometer is explained as the ophthalmic apparatus for performing various simulations on the vision in the examinee's eye, but the present disclosure is not necessarily limited thereto. For instance, the subjective optometric device exemplified in the second embodiment may serve as an ophthalmic apparatus to simulate the vision in the examinee's eye. As another alternative, an apparatus provided separately from both the ocular aberrometer and the subjective optometric device may serve as an ophthalmic apparatus to simulate the vision in the examinee's eye. As such an apparatus, for example, a general-purpose computer (a personal computer and others) may be utilized. In any case, the measurement program including each processing shown in the flowchart of FIG. 2 or each processing shown in the flowchart of FIG. 6 and others are stored in the memory, and that program is executed by the processor. When the ophthalmic apparatus is not provided with the structure of the ocular aberrometer, for instance, the apparatus may be configured to obtain the wavefront aberration data by reading in the naked-eye wavefront aberration data measured by the ocular aberrometer by data transmission or reading from a memory card having the wavefront aberration data stored therein. When each of the foregoing processings is carried out by use of the wavefront aberration data, even the ophthalmic apparatus provided separately from the ocular aberrometer can perform the simulation similar to that in the above embodiments and display a simulation result on the monitor integral with the ophthalmic apparatus or a monitor connected to the ophthalmic apparatus. The naked-eye wavefront aberration data utilizable in the simulation is not limited to the naked-eye wavefront aberration $W(\rho, \theta)$. For instance, it may be the data representing coefficients (e.g., coefficients of the Zernike polynomials) of the polynomials that approximate the wavefront aberration data. Specifically, even when the data representing the coefficients of the polynomials is transmitted from the aberrometer to the ophthalmic apparatus, the simulation can be performed.

In the first and second embodiments, when a final prescription value by the subjective examination is obtained, the CPU 30 may cause the monitor 50 to selectively or in parallel display the evaluation index representing the vision in the examinee's eye in the refractive value corrected state (i.e. the first evaluation index in the first embodiment or the first evaluation index in the initial state in the second embodiment) and the evaluation index representing the vision in the prescription value corrected state. This allows the examiner to compare the vision in the examinee's eye in the refractive value corrected state and the vision in the examinee's eye in the initial state of the subjective examination to objectively grasp how much the quality of vision is improved. In this case, when the evaluation parameters are to be generated as respective evaluation indexes, it is preferable that the evaluation parameters are the same in type (i.e. calculation method) as each other.

In each of the foregoing embodiments, the subjective value in a photopic (daylight) vision state and the subjective value in a mesopic (twilight) vision state may be measured separately. In this case where the subjective value in the photopic vision state and the subjective value in the mesopic vision state are to be measured, the naked-eye wavefront aberration data to be used in each simulation may also be determined in correspondence with different pupil diameters.

In each of the foregoing embodiments, the second correction power in the subjective examination is explained as being different only in at least one of the S, C, and A components by a predetermined amount from the first correction power, but the present disclosure is not limited thereto. The second correction power has only to be different from the first correction power in any of the low-order aberration components by a predetermined amount. For instance, the second correction power may be different from the first correction power in prism power.

What is claimed is:

1. A method of evaluating quality of vision in an examinee's eye, comprising:
    an aberration data obtaining step of obtaining naked-eye wavefront aberration data of the examinee's eye measured by an ocular aberrometer;
    a first evaluation index generating step of: calculating, based on the naked-eye wavefront aberration data and a first correction power, first corrected wavefront aberration data of the examinee's eye intended for a prescription with the first correction power; and generating a first evaluation index based on the first corrected wavefront aberration data, the first evaluation index representing the quality of vision in the examinee's eye intended for the prescription with the first correction power;
    a second evaluation index generating step of: calculating, based on the naked-eye wavefront aberration data and a second correction power, second corrected wavefront aberration data of the examinee's eye intended for a prescription with the second correction power, the second correction power being different from the first correction power in at least one component of spherical power (S), astigmatic power (C), and astigmatic axis angle (A); and generating a second evaluation index based on the second corrected wavefront aberration data, the second evaluation index representing the quality of vision in the examinee's eye intended for the prescription with the second correction power; and
    a display control step of displaying the first evaluation index and the second evaluation index selectively or in parallel on a monitor.

2. The method of evaluating quality of vision in an examinee's eye according to claim 1,
    wherein the second evaluation index generating step includes generating the second evaluation index corresponding to each of two or more different second correction powers, and
    wherein the display control step includes displaying the respective second evaluation indexes separately or in parallel on the monitor.

3. The method of evaluating quality of vision in an examinee's eye according to claim 2,
    wherein the second evaluation index generating step includes setting, as the second correction powers, a plus second correction power corresponding to a correction power in which at least one component of the S, C, and A is increased by a predetermined amount with respect to the first correction power and a minus second correction power corresponding to a correction power in which at least one component of the S, C, and A is decreased by a predetermined amount with respect to the first correction power, and
    the second evaluation index based on the plus second correction power and the second evaluation index based on the minus second correction power are separately generated.

4. The method of evaluating quality of vision in an examinee's eye according to claim 3, wherein the second evaluation index generating step includes setting, as the second correction powers, a plus second correction power corresponding to a correction power in which an astigmatic axis angle is rotated by a predetermined amount in a positive direction with respect to the first correction power, and a minus second correction power corresponding to a correction power in which an astigmatic axis angle is rotated by a predetermined amount in a negative direction with respect to the first correction power, and generating the respective second evaluation indexes.

5. The method of evaluating quality of vision in an examinee's eye according to claim 1, further comprising a condition obtaining step of obtaining an examination condition based on an operation signal input to an input interface, the examination condition being set in a subjective optometric device configured to switch refractive power of an optical member to be placed in front of the examinee's eye to subjectively measure a correction power of the examinee's eye, and
    wherein the first evaluation index generating step includes applying the examination condition to the first correction power to generate the first evaluation index, and updating the first evaluation index in sync with a change in the examination condition by the input interface.

6. The method of evaluating quality of vision in an examinee's eye according to claim 4, wherein the second evaluation index generating step includes applying a correction power, in which a predetermined SCA component is added to the examination condition, to the second correction power to generate the second evaluation index, and updating the second evaluation index in sync with a change in the examination condition by the input interface.

7. The method of evaluating quality of vision in an examinee's eye according to claim 1,
    wherein the first evaluation index generating step includes applying an objective eye refractive value (a REF value) based on the naked-eye wavefront aberration data to the first correction power to generate the first evaluation index, and
    wherein the second evaluation index generating step includes applying a correction power, in which a predetermined SCA component is added to the objective eye refractive power, to the second correction power to generate the second evaluation index.

8. A method of evaluating quality of vision in an examinee's eye, comprising:
    an aberration data obtaining step of obtaining naked-eye wavefront aberration data of an examinee's eye measured by an ocular aberrometer;
    a condition obtaining step of obtaining an examination condition based on an operation signal input to an input interface, the examination condition being set in a subjective optometric device configured to switch a position of an optical member to be placed in front of the examinee's eye to subjectively measure a correction power of the examinee's eye; and an evaluation index generating step of: calculating, based on the naked-eye wavefront aberration data and a correction power, corrected wavefront aberration data of the examinee's eye intended for a prescription with the correction power corresponding to the examination condition by use of the naked-eye wavefront aberration data; and generating an evaluation index based on the corrected wavefront aberration data, the evaluation index representing the quality of vision in the examinee's eye intended for the prescription with the correction power, and the evaluation index generating step including updating the evaluation index in sync with a change in the examination condition by the input interface.

9. The method of evaluating quality of vision in an examinee's eye according to claim 8, the method being to be executed by an ophthalmic apparatus provided with a switching unit configured to switch an optical member to be placed in front of the examinee's eye, and a controller including a display part configured to display the evaluation index, and the input interface.

10. A storage medium storing an ophthalmic measurement program to simulate an evaluation index representing quality of vision in an examinee's eye,
wherein the ophthalmic measurement program is executed by a processor of an ophthalmic apparatus to cause the ophthalmic apparatus to perform:
an aberration data obtaining step of obtaining naked-eye wavefront aberration data of the examinee's eye;
a first evaluation index generating step of: calculating, based on the naked-eye wavefront aberration data and a first correction power, first corrected wavefront aberration data of the examinee's eye intended for a prescription with the first correction power; and generating a first evaluation index based on the first corrected wavefront aberration data, the first evaluation index representing the quality of vision in the examinee's eye intended for the prescription with the first correction power;
a second evaluation index generating step of: calculating, based on the naked-eye wavefront aberration data and a second correction power, second corrected wavefront aberration data of the examinee's eye intended for a prescription with the second correction power, the second correction power being different from the first correction power in at least one component of spherical power (S), astigmatic power (C), and astigmatic axis angle (A); and generating a second evaluation index based on the second corrected wavefront aberration data, the second evaluation index representing the quality of vision in the examinee's eye intended for the prescription with the second correction power; and
a display control step of displaying the first evaluation index and the second evaluation index selectively or in parallel on a monitor.

11. A subjective optometric device comprising:
a controller; and
a processor,
wherein the controller includes: a switching unit configured to switch an optical member to be placed in front of an examinee's eye; a display part; and an input interface to be operated to change the optical member to be placed, and
wherein the processor is configured to execute:

a first evaluation index generating step of generating a first evaluation index based on at least a first correction power, the first evaluation index representing the quality of vision in the examinee's eye intended for a prescription with the first correction power;
a second evaluation index generating step of generating a second evaluation index based on at least a second correction power different from the first correction power in at least one component of spherical power (S), astigmatic power (C), and astigmatic axis angle (A), the second evaluation index representing the quality of vision in the examinee's eye intended for a prescription with the second correction power, the quality of vision being different from the quality of vision represented by the first evaluation index; and
a display control step of displaying the first evaluation index and the second evaluation index selectively or in parallel on a monitor of the display part.

12. The subjective optometric device according to claim 11,
wherein the processor is configured to:
further execute an obtaining step of obtaining an objective eye refractive value (a REF value) of the examinee's eye; and
apply the objective eye refractive value to the first correction power in the first evaluation index generating step to generate the first evaluation index.

13. The subjective optometric device according to claim 11,
wherein the processor is configured to:
switch refractive power of the optical member based on an operation of the input interface to set an examination condition; and
apply the examination condition to the first correction power in the first evaluation index generating step to generate the first evaluation index, and update the first evaluation index in sync with a change in the examination condition by the input interface.

14. The subjective optometric device according to claim 13,
wherein the processor is configured to apply a correction power, in which a predetermined SCA component is added to the examination condition, to the second correction power to generate the second evaluation index in the second evaluation index generating step, and update the second evaluation index in sync with a change in the examination condition by the input interface.

15. The subjective optometric device according to claim 11,
wherein the processor is configured to execute:
the second evaluation index generating step including:
setting, as the second correction powers, a plus second correction power corresponding to a correction power in which at least one component of the S, C, and A is increased by a predetermined amount with respect to the first correction power and a minus second correction power corresponding to a correction power in which at least one component of the S, C, and A is decreased by a predetermined amount with respect to the first correction power, and
separately generating the second evaluation index based on the plus second correction power and the second evaluation index based on the minus second correction power, and the display control step including displaying the second evaluation indices selectively or in parallel on the monitor.

\* \* \* \* \*